(12) United States Patent
Ueberle (10) Patent No.: US 7,267,659 B2
(45) Date of Patent: Sep. 11, 2007

(54) METHOD AND APPARATUS FOR TRANSFERRING MEDICALLY EFFECTIVE SUBSTANCES INTO CELLS

(75) Inventor: Friedrich Ueberle, Oststeinbek (DE)

(73) Assignee: Dornier MedTech Systems GmbH, Wessling (DE)

( * ) Notice: Subject to any disclaimer, the term of this patent is extended or adjusted under 35 U.S.C. 154(b) by 540 days.

(21) Appl. No.: 10/445,378

(22) Filed: May 23, 2003

(65) Prior Publication Data
US 2004/0039329 A1 Feb. 26, 2004

(30) Foreign Application Priority Data
May 24, 2002 (DE) ................. 102 23 196

(51) Int. Cl.
A61B 17/20 (2006.01)
(52) U.S. Cl. ....................................... 604/22
(58) Field of Classification Search ............ 604/19, 604/20, 22; 600/458, 439; 424/450, 951; 601/2–4; 514/44; 435/458
See application file for complete search history.

(56) References Cited

U.S. PATENT DOCUMENTS

| | | |
|---|---|---|
| 2,578,505 A | 12/1951 | Carlin |
| 2,707,391 A | 5/1955 | McSkimin |
| 3,406,302 A | 10/1968 | Lanyi |
| 3,934,458 A | 1/1976 | Beretsky et al. |
| 3,946,829 A | 3/1976 | Mori et al. |
| 4,240,285 A | 12/1980 | Langdon |
| 4,369,100 A | 1/1983 | Sawyer |
| 4,586,512 A | 5/1986 | Do-huu |
| 4,620,546 A | 11/1986 | Aida |
| 4,658,828 A | 4/1987 | Dory |
| 4,671,254 A | 6/1987 | Fair |
| 4,712,037 A | 12/1987 | Verbeek et al. |
| 5,318,014 A | 6/1994 | Carter |
| 5,395,592 A | 3/1995 | Bolleman |
| 5,474,531 A | 12/1995 | Carter |
| 5,498,421 A | 3/1996 | Grinstaff |
| 5,524,620 A | 6/1996 | Rosenschein |
| 5,531,980 A | 7/1996 | Schneider |
| 5,543,553 A | 8/1996 | Stein |
| 5,567,414 A | 10/1996 | Schneider |
| 5,635,207 A | 6/1997 | Grinstaff |
| 5,639,473 A | 6/1997 | Grinstaff |
| 5,643,553 A | 7/1997 | Schneider |
| 5,650,156 A | 7/1997 | Grinstaff |
| 5,658,551 A | 8/1997 | Schneider |
| 5,658,992 A | 8/1997 | Ehlers |

(Continued)

FOREIGN PATENT DOCUMENTS

WO WO91/00358 1/1991

(Continued)

Primary Examiner—Manuel Mendez
(74) Attorney, Agent, or Firm—King & Spalding LLP (57) ABSTRACT

A method and a apparatus for transferring medically effective substances in the form of molecules, such as DNA, oligos, certain chemicals, etc., into the living cells of humans, animals and/or plants using acoustic energy or through cavitation which is produced by acoustic energy in vitro, ex vivo and in vivo. Via suitable sensors, the lifetime of the cavitation bubbles is determined or specified, which then for its part acts as the criterion or the function for controlling the acoustic intensity and thus also the cavitation intensity.

30 Claims, 5 Drawing Sheets

U.S. PATENT DOCUMENTS

| | | |
|---|---|---|
| 5,665,382 A | 9/1997 | Grinstaff |
| 5,665,383 A | 9/1997 | Grinstaff |
| 5,795,581 A | 8/1998 | Segalman |
| 6,039,565 A | 3/2000 | Chou et al. |
| 6,203,777 B1 | 3/2001 | Schroder |
| 6,206,835 B1 | 3/2001 | Spillman |
| 6,298,264 B1 | 10/2001 | Zhong |
| 6,361,747 B1 | 3/2002 | Dion |
| 6,416,740 B1 | 7/2002 | Unger |
| 6,424,863 B1 | 7/2002 | Flock |
| 6,428,532 B1 | 8/2002 | Doukas |
| 6,443,898 B1 | 9/2002 | Unger |
| 6,444,192 B1 | 9/2002 | Mattrey |
| 6,444,217 B1 | 9/2002 | Kwok |
| 6,461,586 B1 | 10/2002 | Unger |
| 6,465,006 B1 | 10/2002 | Zhang |
| 2003/0017578 A1 | 1/2003 | Ueberle |

FOREIGN PATENT DOCUMENTS

| | | |
|---|---|---|
| WO | WO96/20784 | 7/1996 |
| WO | WO99/13943 | 3/1999 |
| WO | WO99/42039 | 8/1999 |
| WO | WO99/42176 | 8/1999 |
| WO | WO 00/02588 | 1/2000 |
| WO | WO 00/38580 | 7/2000 |
| WO | WO 00/69942 | 11/2000 |
| WO | WO 00/76406 | 12/2000 |
| WO | WO 01/48181 | 7/2001 |
| WO | WO 02/051501 | 7/2002 |

METHOD AND APPARATUS FOR TRANSFERRING MEDICALLY EFFECTIVE SUBSTANCES INTO CELLS

CROSS-REFERENCE TO RELATED APPLICATION

This application claims priority to co-pending German patent application No. 102 23 196.6, which was filed on May 24, 2002 and is incorporated herein by reference.

FIELD OF THE INVENTION

The invention generally relates to the application of acoustic energy pulses to living tissue, and more particularly, to transferring medically effective substances into cells.

BACKGROUND OF THE INVENTION

An existing approach for the transfer of molecules into cells of life forms is described in the PCT application with International Publication Number WO 01/48181 A2, which is incorporated herein by reference. The existing approached described therein relates to the transfer of molecules into cells, whereby a medium carrying the molecules to be transferred and the target cells can be exposed to acoustic pulses in the focusing area of a source of acoustic pulses.

In light of the foregoing existing approach, there is a need in the art to further control cavitation in a simple and reliable manner when transferring medically effective substances into cells.

SUMMARY OF THE INVENTION

According to the present invention, there is provided a method and a device for transferring medically effective substances into cells. According to one aspect of the invention this is achieved by transferring medically effective substances (agents) in the form of molecules—such as DNA, oligos, certain chemicals, etc.—into the living cells of humans, animals and/or plants using acoustic energy or through cavitation which is produced by this, in vitro, ex vivo and in vivo by means of suitable sensors—especially by means of acoustic sensors—the lifetime of the cavitation bubbles is determined, which then, for its part, acts as the criterion or the function for controlling the acoustic intensity and thus also the cavitation intensity. The invention is based on the understanding that as regards the cavitation bubbles the time between their creation and their collapse is a direct indicator for the energy transformed in the cavitation bubbles. This means that by determining or specifying the lifetime of the cavitation bubbles the energy to be used optimally for the associated transfection of target cells can be reliably controlled.

According to another aspect of the invention, it is proposed that a sound transformer is combined or fitted with sensors which are able to detect the acoustic signals created particularly when cavitation bubbles collapse, to forward them to a device that converts them to electric signals which then permit, for their part, direct conclusions to be drawn as regards cavitation activity.

According to another aspect of the invention, an apparatus for transferring medically effective substances in the form of molecules into living cells of humans, animals and/or plants in vitro, ex vivo and/or in vivo, includes an acoustic transformer, an electronic system connected to at least one sensor, and a medium for sound transmission in which the molecules to be transferred and the target cells are located in the focusing area of the acoustic transformer where the target cells can be exposed to specific acoustic pulses generating the cavitation, wherein the acoustic transformer is connected with the electronic system which is arranged for detecting of the collapse times of the cavitation bubbles and for controlling the acoustic transformer as a function of the collapse times. From the evaluation of the acoustic signals recorded, not only the cavitation activity but also the lifetime of the cavitation bubbles, the location of their creation, and the position of test tubes etc. can be determined.

In addition, the signals recorded within the scope of the invention can also be evaluated to provide images from which the precise location of cavitations and acoustic concentrations can be recognised, e.g. on a plant leaf that has been brought in, which also means that the position of the transfected cells is known. It is also possible to regulate the control function and/or strength of the pulse sequence in order to optimise the effect when transfecting cells. The acoustic signals are triggered via a control device, which, for example, can also program certain series, pulse numbers etc. or offers a presetting.

The method according to the invention can be further optimised by the additional provision of a thermosensor. In general, the thermosensors can be arranged to monitor the medium in which the cells to be treated and molecules are to be found in order to prevent overheating or to perform application of sound at a specific temperature. The thermosensor allows the exact determination of the specimen temperature so that the temperature of the surrounding liquid can be maintained or controlled or that the pulse parameters (follow-on frequency, burst length, amplitude) can be set in such a way that the sensitive cells are not overheated. In this way, it is also possible to keep the item to be subjected to sound initially below temperature—e.g. with cold water or similar, or even, if necessary, with liquid nitrogen—and only to warm the required target point specifically through the sound signals. A suitable signal sequence can also be generated, which initially causes the warming through superposition and triggers the transfecting acoustic signals at the right moment. In the case of a liquid with known properties, particularly with regards to the degree of oxygen contained therein, such as viscosity and purity, typical collapse times for the cavitation bubbles can be empirically determined as a function of the intensity of the acoustic transformers. These measured values can then be used as base values for practical applications. In an alternate case, it is also possible, on the basis of the collapse times determined, to draw conclusions about the state or the properties of particular liquids. Additionally, cavitation can be further controlled in liquids, since cavitation can be impeded or prevented by excess pressure in liquids.

These and other aspects of the invention will be described further in the detailed description below in connection with the drawings and the claims.

BRIEF DESCRIPTION OF THE DRAWINGS

The accompanying drawings are incorporated into and form a part of the specification for the purpose of explaining the principles of the invention. The drawings are not to be construed as limiting the invention to only the illustrated and described examples of how the invention can be made and used. Further features and advantages will become apparent from the following, and more particular description of the invention as illustrated in the accompanying drawings, wherein.

DETAILED DESCRIPTION OF THE INVENTION

The illustrative embodiments of the present invention will be described with reference to the drawings, wherein like elements and structures are indicated by like reference numbers. According to exemplary embodiments of the present invention, effective substances (agents) in the form of molecules, such as DNA, oligos, certain chemicals, etc., can be medically transferred into the living cells of humans, animals and/or plants using acoustic energy or through cavitation which is produced by acoustic energy, in vitro, ex vivo and in vivo, by means of suitable sensors. Features of the exemplary embodiments of the present invention include: 1) the source has a line-shaped focusing area in which the acoustic pulses exceed a specific pressure or negative pressure and/or a specified intensity; 2) a hollow cylindrical device is provided into which a large number of in-phase acoustic pulses are passed radially from the outside, whereby, in the area around the rotational axis of the hollow cylinder, a reproducible zone of transient cavitation events is generated; 3) a further device is provided through which a relative movement between the medium and the focusing area can be arranged.

Typically, the target cells to be treated are made, through cavitation, temporarily permeable to the molecules of the medical substances to be transferred. Care should be taken to ensure here that the cavitation is controlled as efficiently as possible, i.e. the target cells should be made just sufficiently temporarily permeable through the cavitation, which means that they should not by any means be damaged by an excess control of cavitation, and in particular they should not be permanently damaged or even destroyed.

Figure 1:
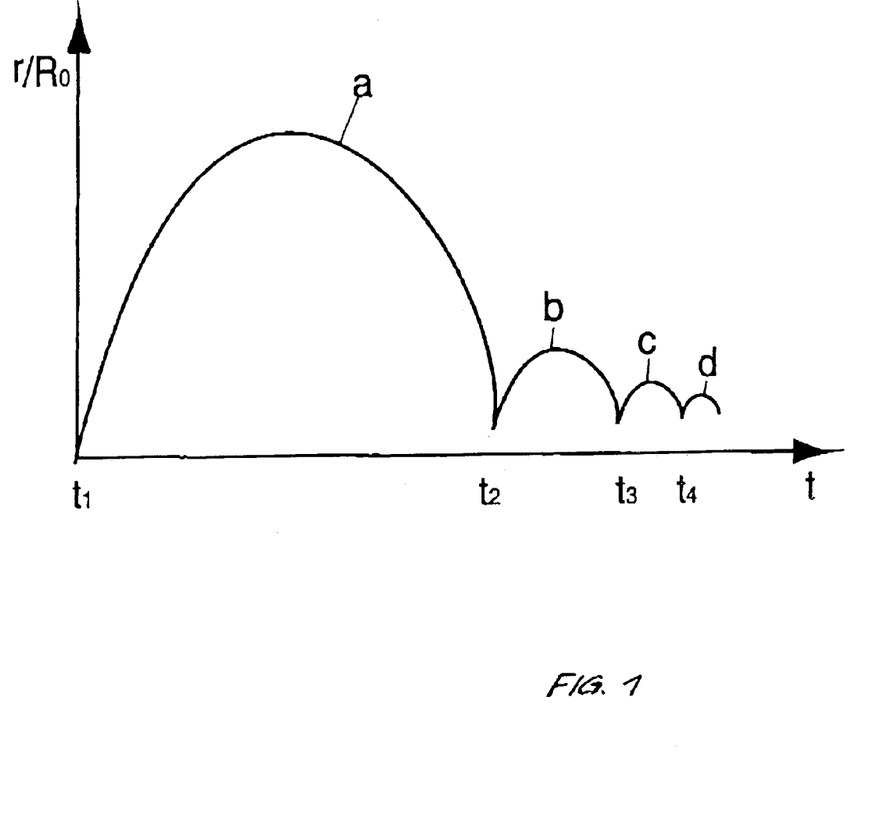
FIG. 1 is showing a schematic diagram of the basic radius of a cavitation bubble over time, from its creation to its collapse, with the increasingly small cavitation bubbles in sequence.

Referring to FIG. 1, a cavitation bubble occurs at the point in time $t_1$. Until its collapse at the point in time $t_2$, its radius corresponds to the curve a over the time t, whereby here in concrete terms the relative cavitation bubble radius r in relation to the radius $R_0$ of the bubble nucleus is shown as a function of the time t. A cavitation bubble is created at the point in time $t_1$ through the impact of the acoustic wave on a bubble nucleus in the medium 2a (see FIG. 2) or through the exceeding of the cavitation threshold at the corresponding acoustic intensity. The cavitation bubble occurring at $t_1$ collapses again at the point in time $t_2$. Smaller and smaller cavitation bubbles with the curves b, c, d, etc. are created following the bubble that collapsed in each case before them, in each case through the energy released during the collapse.

Basically, it can be determined that as the radius of a cavitation bubble increases, its lifetime also increases. In other words, this means that cavitation bubbles with larger radii and a correspondingly greater energy content thus collapse later. Accordingly, the collapse time is an analogous indicator of the energy converted in the cavitation bubble in question.

Figure 2:
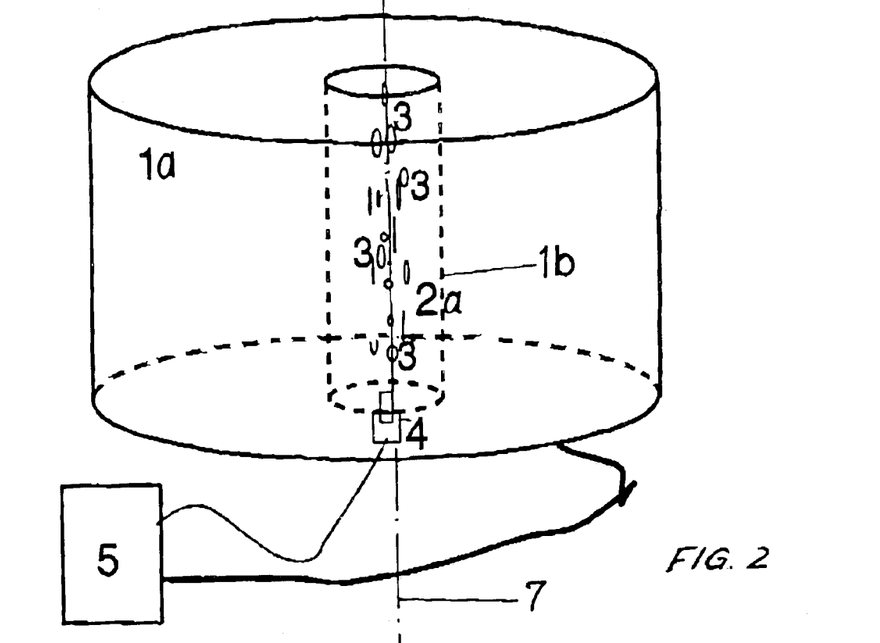
FIG. 2 is showing a schematic diagram of a device for execution of the method according to the invention with a cylindrical acoustic transformer.

FIG. 2 shows an acoustic transformer 1a which has inside it, in a homogenous cylindrical layout, for example, a large number of piezo elements not shown separately, the lines of force of which meet in the area of the central middle line 7 of the acoustic transformer 1a. This means that the middle line 7 also at the same time forms the central line of a line focusing area inside the cylindrical hollow space 1b of the acoustic transformer 1a. When sound is applied by the latter, cavitation bubbles can thus be formed along the focusing area in the medium 2a. The medium 2a may be located directly in the hollow space 1b or in a test tube placed in this hollow space. Cells to be treated and/or molecules 3 are placed in the medium 2a which can be exposed within the scope of the invention to an extremely precisely measurable application of sound. The collapse times of the cavitation bubbles occurring as a result are detected by a sensor 4, which forwards its signals to an electronic unit 5 for the control of the acoustic transformer 1a.

Figure 3:
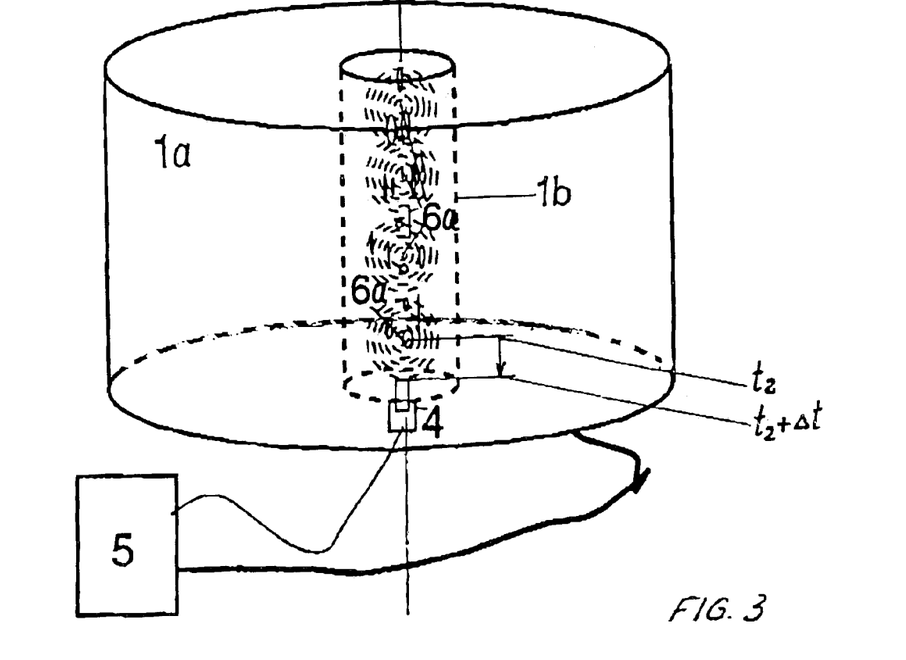
FIG. 3 is showing a schematic diagram of the device according to FIG. 2 in a different sound application state.

The apparatus according to FIG. 2 is in the state not subjected to sound. At the moment when a cavitation bubble collapses, an acoustic signal 6a is emitted according to FIG. 3 which, as also can be seen from FIG. 3, reaches, after the time $t_2+\Delta t$, a sensor 4, which forwards it to the electronic unit 5 for further processing. The sound transformer is combined or fitted with sensors 4, which are acoustic sensors, which are able to detect the acoustic signals created when the cavitation bubbles collapse and to forward the acoustic signals to the electronic unit 5 which converts the acoustic signals to electric signals which then permit, for their part, direct conclusions to be drawn as regards cavitation activity. On the basis of laboratory tests, it can be determined that the line focusing area with the middle line 7 has a diameter of approx. 2 mm. Consequently, the receptacles, for example a test tube made from acoustically conductive plastic, e.g. polyurethane, in which the medium 2a with the target cells and/or molecules 3 to be transferred has been placed, should have a maximum diameter of only 3-4 mm, so that, when sound is applied, as many target objects as possible are reached. The latter is also facilitated by the fact that during sound application a certain turbulence is created by these in the medium 2a. Furthermore, the acoustic transformer of FIG. 2 is formed and arranged in such a way to also perform as a sensor. Therefore, the acoustic transformer is arranged to be switched over manually or automatically from an acoustic transformer function to an acoustic sensor function and from the acoustic sensor function to the acoustic transformer function.

Figure 4:
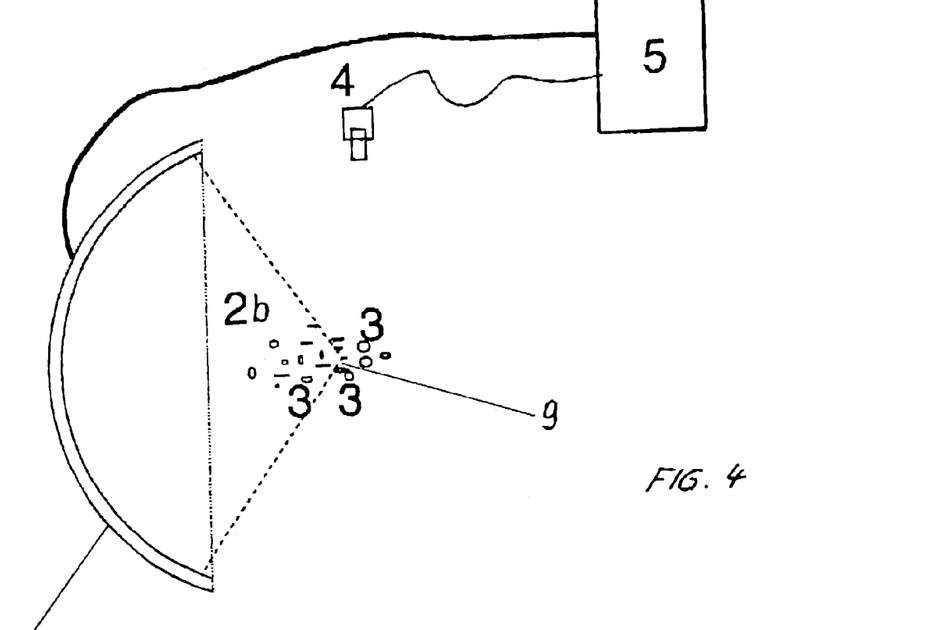
FIG. 4 is showing a schematic diagram of a device for execution of the method according to the invention with a shell-shaped acoustic transformer.

The apparatus according to FIG. 4 has a shell-shaped preferably concave shaped acoustic transformer 8 whose lines of force focus point-shaped in the area 9. When the medium 2b is subjected to an application of sound according to FIG. 5 during which cavitation bubbles are formed, then the acoustic signals 6b emitted by the collapsing cavitation bubbles once again reach the sensor 4 after a time $t_2+\Delta t$. The acoustic transformer 8 can be fitted with piezo elements in a homogenous layout or also be realised in the form of a so-called indentation EMSE. A magnetostrictive acoustic transformer would also be conceivable here.

Figure 6:
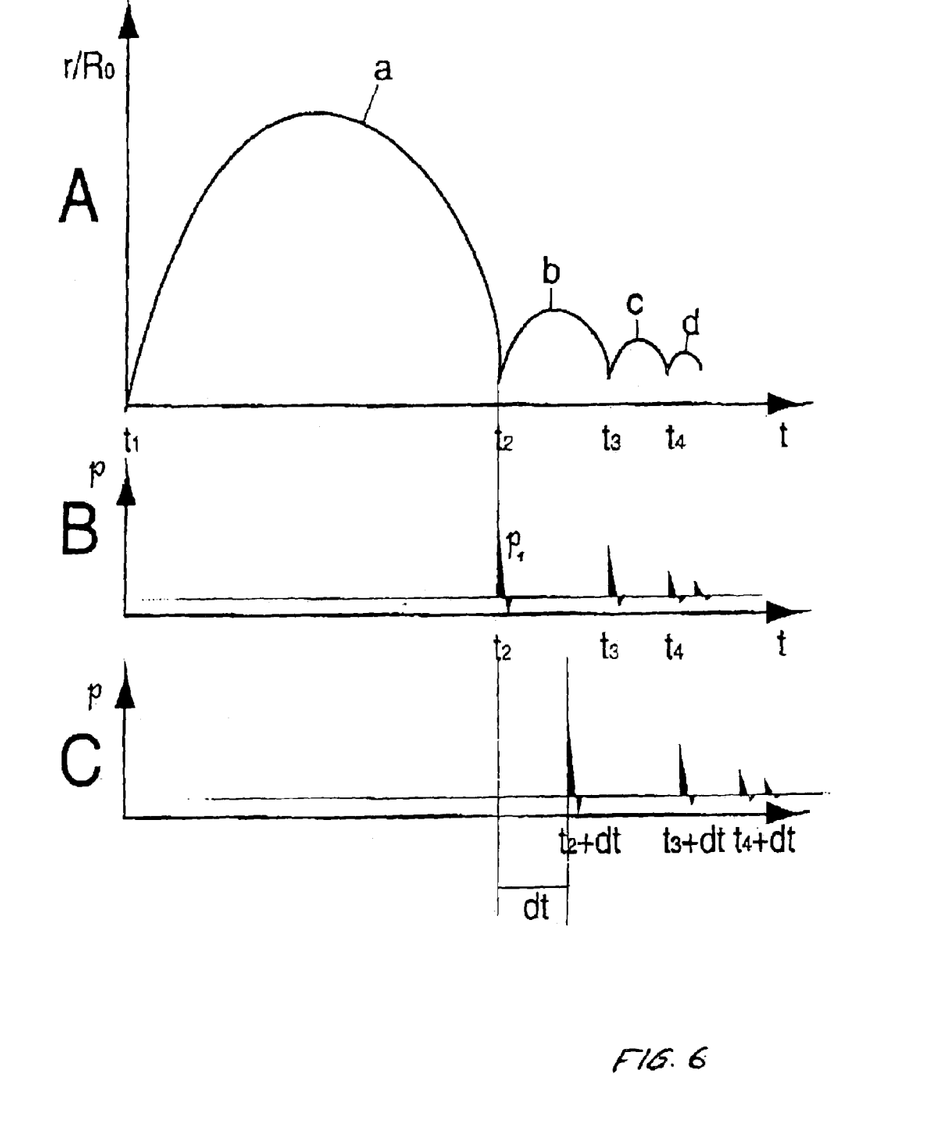
FIG. 6 is showing a schematic diagram of the development or the course of the relative radii of the cavitation bubbles over time in Part A; Part B, by means of a pressure/time diagram, how, simultaneously with the collapsing cavitation bubbles according to Part A, new shock waves are released or created; Part C, finally, diagrammatically at what times the collapse signals can be received at the location of the sensors.

In FIG. 6, Part A shows the relative cavitation bubble radius r, in relation to the radius of the bubble nucleus $R_0$ as a function of the time t. It can be assumed that the bubble radii $R_0$ are very similar after just a few sound pulses and thus that a fairly standard collapse time for all bubbles is achieved. At the point in time $t_1$, the bubble is stimulated by an acoustic pulse, for example, by a shock wave, and thus enlarges its radius. Gas dissolved in the liquid and vapour from the liquid diffuse thereby into its inside. After a time which depends both on the ambient conditions, for example, the static pressure and the viscosity, and on the stimulating pulse, the bubble radius shrinks with increasing speed and the bubble collapses at the point in time $t_2$.

At the moment of collapse $t_2$ the built-up energy is released in part in the form of a shock wave. This is graphically illustrated in Part B of FIG. 6 at the end of bubble a at the point in time $t_2$ as pressure impact $p_1$. The shock wave created as a result spreads as a spherical sound wave in the medium and reaches the measurement sensor at the point in time $t_2+\Delta t$. This is fitted at a distance x from the position of the expected bubble collapse. The collapse signals therefore reach it after a time $\Delta t=x/c$, where c is the speed of the sound in the medium. The collapse signals at the position of the sensor are shown in Part C of FIG. 6. Depending on the nature of the medium, the sequence of radius enlargement and collapse may be repeated several times whereby, as with a bouncing ball, less and less energy is available for the bubble in question, as a result of the attenuation effects and emission losses, so that the radius and the time to the next collapse in each case become smaller and smaller.

Figure 5:
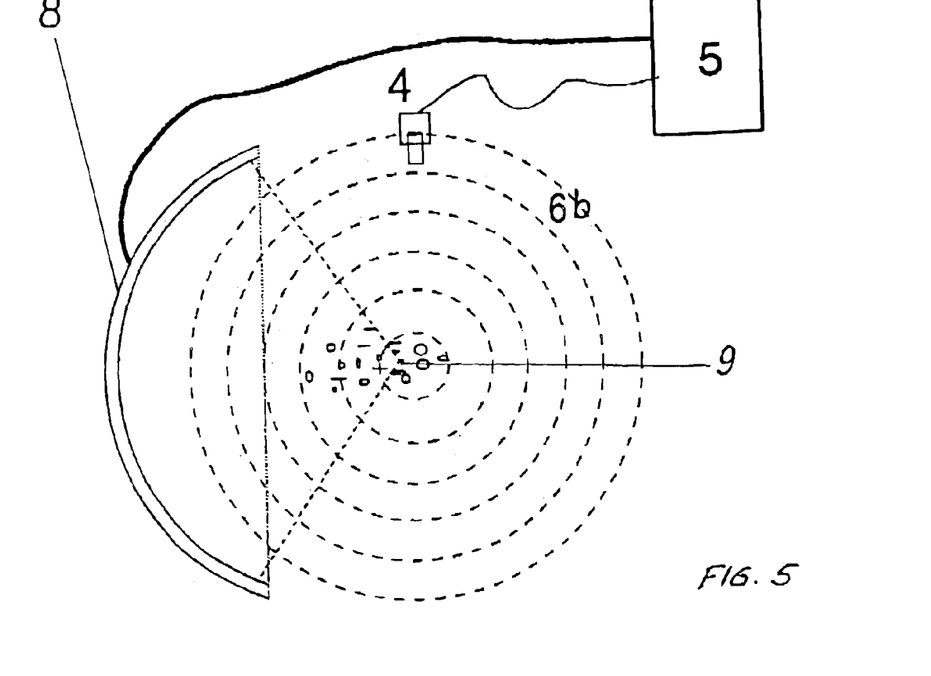
FIG. 5 is showing a schematic diagram of the device according to FIG. 4 in a different sound application state.

With an apparatus with a focussed transformer as shown in FIGS. 4 and 5, the locations of cavitations are generally limited to the focusing area of the sound source and thus approximately at the same distance from the sensor. This gives a very short acoustic signal. In the event of the line-shaped focus according to FIGS. 2 and 3, if the sensor is positioned near to the axis, the collapse signals from the bubbles will arrive at the sensor at different times. In this case, a longer lasting, noise-type collapse signal is received. Here, the time when this signal starts merely needs to be evaluated according to the invention, since it can be expected that it comes from a bubble very close to the sensor and that most of the other bubbles will be formed and collapse again at roughly the same time.

The following description relates to a layout with focused acoustic transformer (focus distance 200 mm) according to FIG. 4. The acoustic transformer of FIG. 4 is formed and arranged in such a way to also perform as a sensor. Therefore, the same acoustic transformer used to create the sound pulses leading to cavitation is also used to receive the cavitation signals. Furthermore, the acoustic transformer is arranged to be switched over manually or automatically from an acoustic transformer function to an acoustic sensor function and from the acoustic sensor function to the acoustic transformer function. Using a high-voltage scanner head, it is possible to follow the course of the voltage at the piezo transformer. Because the piezo elements also convert received acoustic signals into voltage signals again, it is possible, for example, to receive echoes of objects in the acoustic field. Since the transformer focuses very strongly, echoes from the focusing region with a large amplitude are mainly reproduced. Similarly, it is possible to receive the pressure waves that are emitted by collapsing cavitation bubbles particularly in the focusing area.

Here, the signal from 256 µs after the triggering of the sound pulses was analysed in particular. This 256 µs corresponds, with a transformer radius of 195 mm and a speed of sound of 1523 m/s (at water temperature 35° C.), precisely to the distance from the transformer surface to the focus and back again. 128 µs after its triggering, the transformer acoustic signal reaches the focus. If the signal is reflected there at an obstacle, it will arrive back at the transformer again accordingly after a further 128 µs.

The time sequence in water, measured, is as follows:

| Time | Signal location | Distance |
| --- | --- | --- |
| 0 | Transformer surface | 0 |
| 128 µs | Focus | 195 mm |
| 258 µs | Transformer surface (1st reflection) | 390 mm |
| 388 +/− 2 µs | Focus | 585 mm |
| 517 +/− 2 µs | Transformer surface (2nd reflection) | 780 mm |
| 644 +/− 2 µs | Focus | 975 mm |

If a gel material is brought into the acoustic path (thickness 80 mm, speed of sound 1465 m/s, attenuation 0.53 dB/cm MHz) between the transformer and the focus, the running times are extended to 132 µs, 264 µs, 392 µs, 528 µs and 658 µs, respectively.

A cavitation bubble is created when the negative pressure exceeds the tear resistance of the water, which is particularly the case in the focus. There, a bubble is created which, depending on its size, will collapse again after a particular time. A shock wave is generated, and the bubble size and thus collapse time depends on its intensity. The acoustic transformer then also receives the bubble collapse, 128 µs later, in accordance with the distance from the point of creation to the transformer.

In a practical example, a cavitation is created in water, which can be proven through measurement of the transformer signals. In pure water, the reflection of the primary wave at the bubbles just being created is initially found after 262 µs. The amplitudes of the signals vary considerably, since the bubble formation is a non-linear, statistical phenomenon. After this, the echo from the water surface, 255 mm from the transformer zenith, initially arrives very weakly after 340 µs, followed by the collapse signal (in the example, after 444 µs,) and, after 530 µs, a signal that can be taken as the repeat echo between the transformer surface and the existing cavitation bubbles in the focus; the sound primarily generated by the bubble was, of course, after the reflection at the transformer after 393 µs back in the focus, where the bubble was still alive (collapse signal at 444 µs comes 178 µs after the formation signal). The fact that the first signal arrives after 262 µs indicates that the cavitation was formed precisely in the geometric focus of the transformer structure at 200 mm.

With the gel cushion in the acoustic path, hardly any echoes from the water surface are visible and the multi echoes are also strongly attenuated. The bubble collapse signal can still be clearly detected. Compared with water, the lower speed of sound in the gel also has a delaying effect.

Figure 7:
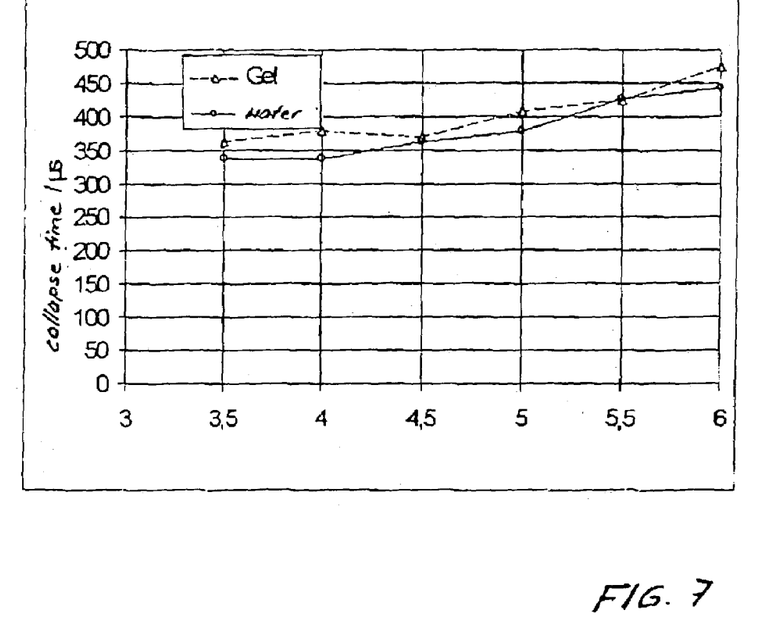
FIG. 7 is showing a schematic diagram of the collapse time as a function of the acoustic transformer control voltage in two different media.
Figure 8:
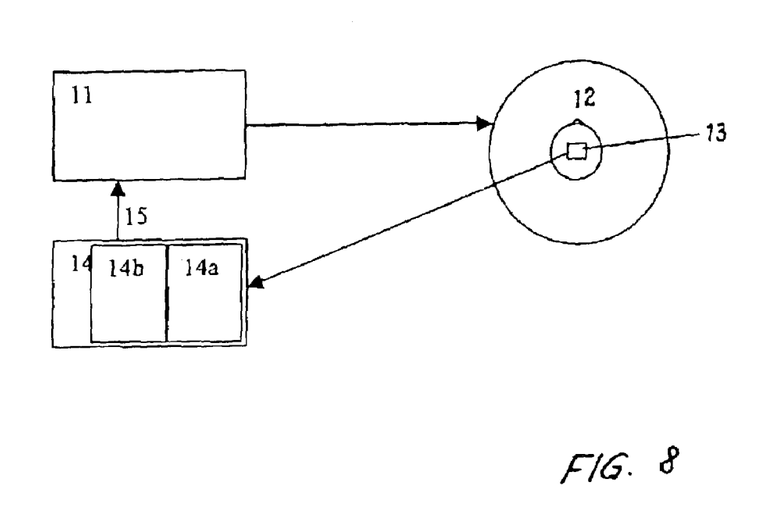
FIG. 8 is showing a schematic diagram of a circuit to control an acoustic transformer.

FIG. 7 shows the collapse time as a function of the transformer control voltage measured in two different media according to the method given above. FIG. 8 shows a block diagram with a circuit 11 to control the acoustic transformer, for example in the form of a pulse circuit. An acoustic transformer 12 has, inside, an acoustic sensor 13 for the collapse signals. An evaluation circuit 14 consists essentially of a pre-amplifier and a time gate 14a and a threshold value switch 14b. A trigger line 15 is used to trigger the control signal for the acoustic transformer.

The method according to the invention can be further optimised by the additional provision of a thermosensor. In general, the thermosensors can be arranged to monitor the medium in which the cells to be treated and molecules are to be found in order to prevent overheating or to perform application of sound at a specific temperature. The thermosensor allows the exact determination of the specimen temperature so that the temperature of the surrounding liquid can be maintained or controlled or that the pulse parameters (follow-on frequency, burst length, amplitude) can be set in such a way that the sensitive cells are not overheated. In this way, it is also possible to keep the item to be subjected to sound initially below temperature—e.g. with cold water or similar, or even, if necessary, with liquid nitrogen—and only to warm the required target point specifically through the sound signals. A suitable signal sequence can also be generated, which initially causes the warming through superposition and triggers the transfecting acoustic signals at the right moment. In the case of a liquid with known properties, particularly with regards to the degree of oxygen contained therein, such as viscosity and purity, typical collapse times for the cavitation bubbles can be empirically determined as a function of the intensity of the acoustic transformers. These measured values can then be used as base values for practical applications. In an alternate case, it is also possible, on the basis of the collapse times determined, to draw conclusions about the state or the properties of particular liquids. Additionally, cavitation can be further controlled in liquids, since cavitation can be impeded or prevented by excess pressure in liquids.

While the invention has been described with respect to the foregoing exemplary embodiments, it will be apparent to those skilled in the art that various modifications, variations and improvements of the invention may be made in light of the above teachings and within the purview of the appended claims without departing from the spirit and intended scope of the invention. In regard to the foregoing description of the exemplary embodiments of the invention, areas which are known to those of ordinary skill in the art have not been described in detail in order to facilitate a clear and concise description of the invention. Accordingly, it should be understood that the invention is not to be limited by the specific exemplary embodiments, but only by the scope of the appended claims.

What is claimed is:

1. An apparatus for transferring medically effective substances in the form of molecules into living cells, comprising:
   an acoustic transformer configured to produce acoustic pulses;
   an electronic system connected to at least one sensor, the electronic system being connected to the acoustic transformer and configured to detect collapse times of cavitation bubbles and to control the acoustic transformer as a function of the collapse times; and
   a medium for sound transmission in which the molecules to be transferred and the living cells are located in a focusing area of the acoustic transformer, wherein the living cells can be exposed to specific acoustic pulses from the acoustic transformer to generate the cavitation bubbles in the medium.

2. The apparatus of claim 1, wherein the acoustic transformer is fitted directly with the at least one sensor, and wherein the at least one sensor comprises an acoustic sensor.

3. The apparatus of claim 1, wherein the acoustic transformer is configured to perform as the at least one sensor.

4. The apparatus of claim 3, wherein the acoustic transformer is operable to be switched from an acoustic transformer function to an acoustic sensor function and from the acoustic sensor function to the acoustic transformer function.

5. The apparatus of claim 1, wherein the acoustic transformer is configured with a central hollow space that surrounds the medium.

6. The apparatus of claim 5, further comprising a circuit that is configured to control the acoustic transformer with a pulse circuit.

7. The apparatus of claim 5, wherein the central hollow space has a maximum diameter of 4 mm.

8. The apparatus of claim 5, wherein the acoustic transformer is fitted directly with the at least one sensor, and wherein the at least one sensor comprises an acoustic sensor.

9. The apparatus of claim 5, wherein the acoustic transformer is configured to perform as the at least one sensor.

10. The apparatus of claim 9, wherein the acoustic transformer is operable to be switched from an acoustic transformer function to an acoustic sensor function and from the acoustic sensor function to the acoustic transformer function.

11. The apparatus of claim 1, further comprising thermosensors, wherein the thermosensors are configured to monitor the temperature of the living cells to prevent overheating of the living cells.

12. The apparatus of claim 11, wherein the acoustic transformer is configured with a central hollow space that accommodates a test tube therein.

13. The apparatus of claim 11, wherein the acoustic transformer is configured with a central hollow space that surrounds the medium.

14. The apparatus of claim 13, wherein the central hollow space has a maximum diameter of 4 mm.

15. The apparatus of claim 13, wherein the acoustic transformer is fitted directly with the at least one sensor, and wherein the at least one sensor comprises an acoustic sensor.

16. The apparatus of claim 13, wherein the acoustic transformer is configured to perform as the at least one sensor.

17. The apparatus of claim 16, wherein the acoustic transformer is configured to be switched from an acoustic transformer function to an acoustic sensor function and from the acoustic sensor function to the acoustic transformer function.

18. The apparatus of claim 13, further comprising a circuit that is configured to control the acoustic transformer with a pulse circuit.

19. The apparatus of claim 1, further comprising thermosensors, wherein the thermosensors are configured to monitor the temperature of the living cells, wherein the acoustic transformer is further controlled based on the monitored temperature.

20. The apparatus of claim 1, wherein the acoustic transformer is configured with a central hollow space that accommodates a test tube therein.

21. The apparatus of claim 1, wherein the acoustic transformer comprises a shell-shape.

22. The apparatus of claim 21, wherein the acoustic transformer is concave shaped.

23. The apparatus of claim 21, wherein the acoustic transformer is fitted directly with the at least one sensor, and wherein the at least one sensor comprises an acoustic sensor.

24. The apparatus of claim 21, wherein the acoustic transformer is configured to perform as the at least one sensor.

25. The apparatus of claim 24, wherein the acoustic transformer is configured to be switched from an acoustic transformer function to an acoustic sensor function and from the acoustic sensor function to the acoustic transformer function.

26. The apparatus of claim 21, further comprising a circuit that is configured to control the acoustic transformer with a pulse circuit.

27. The apparatus of claim 1, further comprising a circuit that is configured to control the acoustic transformer with a pulse circuit.

28. A method for transferring medically effective substances into living cells, comprising the steps of:
   placing living cells in a medium that allows the transmission of sound;
   placing medically effective substances in the form of molecules in the medium;
   applying acoustic pulses to the medium, the acoustic pulses producing cavitation bubbles in the medium;
   detecting collapse times associated with the cavitation bubbles; and
   controlling the applying step based on the collapse times, wherein the acoustic pulses are focused at a focusing area in the medium and wherein the living cells and the molecules are placed in the focusing area in the medium.

29. The method of claim 28, wherein the medically effective substances in the form of molecules comprise at least one of deoxyribonucleic acids and oligos.

30. The method of claim 28, further comprising the step of specifying the lifetime of the cavitation bubbles produced by the acoustic energy.

\* \* \* \* \*